United States Patent [19]
Erhardt

[11] Patent Number: 5,977,409
[45] Date of Patent: Nov. 2, 1999

[54] METHOD OF USING α-SUBSTITUTED BENZYLAMINE CHIRAL AUXILIARY SYNTHETIC REAGENTS

[75] Inventor: Paul W. Erhardt, Sylvania, Ohio

[73] Assignee: University of Toledo, Toledo, Ohio

[21] Appl. No.: 09/059,990

[22] Filed: Apr. 14, 1998

Related U.S. Application Data

[60] Provisional application No. 60/043,603, Apr. 15, 1997.
[51] Int. Cl.$^6$ .................................................. C07B 57/00
[52] U.S. Cl. ............................................ 564/303; 564/302
[58] Field of Search ...................................... 564/302, 303

[56] References Cited

U.S. PATENT DOCUMENTS

| | | | |
|---|---|---|---|
| 5,011,989 | 4/1991 | Yoneyoshi et al. | 564/8 |
| 5,120,853 | 6/1992 | Yoneyoshi et al. | 548/268.4 |

*Primary Examiner*—Brian M. Burn
*Assistant Examiner*—Brian J. Davis
*Attorney, Agent, or Firm*—Emch, Schaffer, Schaub & Porcello, Co., L.P.A.

[57] ABSTRACT

This invention relates to the use of a family of chiral α-substituted benzylamine reagents during chemical synthesis. Specifically, the reagents can be used in an auxiliary manner to deliver either a substituted or unsubstituted nitrogen atom while simultaneously bestowing an asymmetric bias toward the formation and separation of the diastereomeric intermediates that result from reaction of the reagents with racemic substrates also having one or more asymmetric atoms. The chiral auxiliary portion of the reagents can then be readily removed at some later and convenient stage of the overall synthetic scheme. The initial nitrogen-delivery reaction, asymmetric separation procedures, and removal of the chiral auxiliary can all be conducted under routine experimental conditions, including the final debenzylation, such that the overall method is adaptable to large-scale chemistry. Since the reagents are particularly useful whenever a nitrogen-containing system has alpha-, beta- or gamma-asymmetry, the latter being a common structural motif within many pharmaceutical agents, the methods are of primary utility for the laboratory preparation and large-scale manufacture of enantimerically pure drug molecules.

7 Claims, 5 Drawing Sheets

METHOD OF USING α-SUBSTITUTED BENZYLAMINE CHIRAL AUXILIARY SYNTHETIC REAGENTS

RELATED APPLICATION

This application claims the benefit of U.S. Provisional Application No. 60/043,603, filed Apr. 15, 1997, incorporated by reference in its entirety.

FIELD OF THE INVENTION

The present invention relates to methods of using a family of α-substituted benzylamine chiral auxiliary synthetic reagents which have general utility during chemical synthesis for the practical production of nitrogen-containing compounds having enchanced stereochemical purity. After delivering a nitrogen atom in a regiospecific manner while simultaneously bestowing an asymmetric bias to the molecule being synthesized, these reagents can be readily N-debenzylated at some subsequent and convenient step during an overall synthetic process. The methods will be particularly useful whenever a nitrogen-containing system having defined alpha-, beta- or gamma- asymmetry is ultimately desired. The latter is a common structural motif within many pharmaceutical agents. Thus, the methods can be of primary utility for the preparation of enantiomerically pure drug molecules.

BACKGROUND OF THE INVENTION

The rising flow of single-isomer, chiral drugs onto U.S. and world markets is an important trend in today's pharmaceutical industry. In part, this trend has been prompted by the FDA's continuing emphasis to have companies clarify the relationship between a new drug's stereochemical features and its biological effects. It has been estimated that the 1993 worldwide market for single-isomer, chiral drugs reached $35.6 billion, a growth of 22% over 1992. In 1997 the chiral drug market could be as high as $60 billion (S. Stinson, *Chem. & Engin. News*, Sep. 19, 38 (1994)). As a result, practical methods for the production of optically pure synthetic building blocks applicable to the pharmaceutical industry are being heavily researched (R. Noyori, *Asymmetric Catalysis In Organic Synthesis,* John Wiley & Sons, Inc. (1994); D. Ager, *Asymmetric Synthetic Methodology,* CRC Press (1996)). A steady stream of monographs, reviews (*Chem. & Engin. News,* Apr. 24, 37 (1995); *Organic Synthesis,* 401 (1994)), special conferences (Chiral Synthesis Symposium and Workshop, Spring Innovation, Manchester, UK, Apr. 18 (1989); Smith Kline and French Research Symposium: Chirality in Drug Design and Synthesis. Cambridge, UK Mar. 27 (1990); The International Conference on Chirality, Cancun, Mexico, Jun. 6 (1990); Chiral 90, Spring Innovation, Manchester, UK Sep. 18 (1990); Second International Symposium on Chiral Discrimination, Rome, Italy, May 27 (1991)) and new journals (*Chirality,* Vol 1); *Tetrahedron: Asymmetry,* Vol. 1) dedicated to this topic have appeared.

Chiral benzylamine-related systems represent a class of compounds which have considerable potential to be useful as chiral auxiliary reagents. In addition to the common use of the benzyl group as a protecting moiety for oxygen and nitrogen (K. Harada et al. *Bull. Chem. Soc. Jpn.* 46, 1865 (1973)), the N-benzyl system has been shown to be generally useful as a practical means to deliver nitrogen in a regiospecific manner by decreasing the propensity for over alkylation during various synthetic strategies (P. Erhardt, *Synth. Comm.,* 13 (2), 103 (1983)). In these simple structural settings, the benzyl groups are not α-substituted and they quite generally possesss the desirable feature of being able to be readily O- or N-debenzylated at any convenient, subsequent step during an overall synthesis (P. Erhardt, ibid.). Now, when these reagents are additionally α-substituted so as to be made chiral, it follows that any racemic asymmetry present within the reagent's substrate, especially when present in the vicinity near the point of attack by nitrogen, will interact with the auxiliary in a diastereomeric fashion. Thus, this overall approach becomes potentially useful as a general asymmetric method to obtain nitrogen-containing systems which have defined neighboring asymmetry. The latter is a common structural motif within many pharmaceutical drug entities; α- and β-adrenergic agonists and antagonists, HIV protease inhibitors, and numerous antimicrobial agents representing just a few of the many examples.

Although considerable prior art has demonstrated the general utility of using α-unsubstituted benzylamines during synthesis, an extensive literature search reveals that α-substituted, asymmetric benzylamines have been employed in only a very limited number of cases. These cases are now incorporated herein by the following references. In one of these cases, optically pure α-methylbenzylamine was found to react with a racemic epoxide to provide diastereomeric N-alkylated products which were readily separable by column chromatography (R. Kuhlmeyer, et al. *Tetrahedron Lett.,* 25, 3429 (1984)). In another case, optically pure α-methylbenzylamine was reacted with a racemic, substituted cyclohexanone to directly afford an asymmetric synthesis of the corresponding cyclohexanamine in high diastereomeric excess (A. Frahm and G. Knupp, *Tetrahedron Lett.,* 28, 2633 (1981)). These key literature reactions are depicted below in Schemes 1 and 2, respectively, and serve as precedent that the asymmetric elements when placed within the family of reagents that are encompassed by the present invention can, indeed, be expected to be deployed advantageously.

Scheme 1
Specific literature demonstrating an N-alkylation reaction using a chiral benzylamine-related reagent. The asterisk denotes an asymmetric atom. R' = Me.

Scheme 2
Specific literature demonstrating a reductive alkylation reaction using a chiral benzylamine-related reagent. The asterisk denotes an asymmetric atom. R' = Me.

> 92% Diastereomeric Excess

However, a major road-block pertaining to the practical and more general use of these types of chiral reagents, of concern especially during process and manufacturing chemistry, has been the purported inability to subsequently remove the benzyl portion of the reagent (i.e. CHR'Ph) in a convenient manner, such as by routine catalytic hydrogenolysis. This is because when the nitrogen becomes sterically hindered, a situation inherent to the asymmetric versions of such reagents, it is commonly accepted within the present state of the art that the general hydrogenolysis reaction can be expected to be significantly impeded by the presence of the additional steric bulk. The basis for this prevailing view has its origins in the very early chemical literature.

N-debenzylation (cleavage of a carbon-nitrogen bond) has been widely used in chemical synthesis, most often after employing the benzyl as a protecting group for a nitrogen atom within a molecule undergoing other synthetic manipulations. The ease of such debenzylations when undertaken at room temperature and atmospheric pressure increases in the series primary<secondary<tertiary<quaternary ammonium salts (H. Dahn, et al. *Helv. Chim. Acta,* 37, 565 (1954)). However, M. Freifelder was very careful to point out that within any family of amines having the same degree of N-substitution, the steric features of the substituents will also effect the reaction rate and that in particular, difficulty arises when the α-benzyl portion is substituted or hindered (M. Freifelder, *Catalytic Hydrogenation in Organic Synthesis Procedures and Commentary,* John Wiley & Sons (1978)). Likewise, R. Baltzly has previously demonstrated that even a methyl group in the α-position of what would otherwise be a very simple, unhindered system, significantly decreases the rate of hydrogenolysis (R. Baltzly and P. Russell, *J. Am. Chem. Soc.,* 75, 5598 (1953)). Similarly, the effects of a variety of other substituents placed on the aromatic nucleus or in the benzylic position have been studied and, in general, the presence of additional substituents stabilizes these compounds toward hydrogenolysis except for when the groups form more extended aromatic systems (R. Baltzly and J. Buck, *J. Am. Chem. Soc.,* 65, 1984 (1943); R. Baltzly and P. Russell, *J. Am. Chem. Soc.,* 72, 3410 (1950)). For example, the debenzylation of dibenzyl tertiary amine with one of the benzyl rings bearing additional substituents invariably results in the preferential loss of the unsubstituted benzyl group (R. Baltzly and J. Buck, *J. Am. Chem. Soc.,* 65, 1984 (1943)).

Nevertheless, when α-substituted asymmetric benzylamine hydrogenolyses have been forced to occur as part of small scale laboratory studies, the stereochemical course of these reactions are such that inversion of configuration has been observed with both palladium (C. Murchu, *Tetrahedron Lett.,* 38, 3231 (1969); H. Dahn, et al., *Helv. Chim. Acta.,* 53, 1370 (1970); Y. Sugi and S. Mitsui, *Tetrahedron,* 29, 2041 (1973); A. Kieboom and F. Van Rantwijk eds. *Hydrogenation And Hydrogenolysis In Synthetic Organic Chemistry,* Delft University Press, Netherlands, 132 (1977)) and nickel catalysts (Y. Sugi and S. Mitsui, *Tetrahedron,* 29, 2041 (1973); A. Kieboom and F. Van Rantwijk eds. *Hydrogenation And Hydrogenolysis In Synthetic Organic Chemistry,* Delft University Press, Netherlands, 132 (1977)). Two of the most relevant reactions from this body of literature are illustrated in the accompanying Scheme 3 which again provides precedent that the asymmetric nature of these kinds of reagents should be able to be advantageously manipulated, provided that the α-substituted benzyl portions can be conveniently removed in any given specific application.

Scheme 3

Specific literature cases (C. Murchu, Tetrahedron Lett., 38, 3231 (1969); H. Dahn, et al., Helv. Chim. Acta., 53, 1370 (1970); Y. Sugi and S. Mitsui, Tetrahedron, 29, 2041 (1973); A. Kieboom and F. Van Rantwijk eds. Hydrogenation And Hydrogenolysis In SyntheticOrganic Chemistry, Delft University Press, Netherlands, 132-135(1977)) demonstrating debenzylation reactions leading to inversion of stereochemical configuration. For the second reaction R = H, Me, Et (A. Kieboom and F. Van Rantwijk eds. Hydrogenation And Hydrogenolysis In Synthetic Organic Chemistry, Delft University Press, Netherlands, 132-135 (1977)).

Reemphasizing, it has been established that α-substitution lessens the ease of both N-debenzylation and O-debenzylation (R. Baltzly and P. Russell, *J. Am. Chem. Soc.,* 75, 5598 (1953); A. Kieboom, et al., *Journal of catalysis,* 20, 58 (1971)) and that α-alkyl substitution, in particular, causes a far greater degree of difficulty than when similar substitutions are effected on the aryl moiety (M. Freifelder, *Practical Catalytic Hydrogenation,* John Wiley & Sons (1971)). This general assessment for the process of debenzylation is widely acknowledged and is routinely accepted as an overall limitation during consideration of possible synthetic strategies (A. Bellamy, *Tetrahedron*, 16, 4711 (1995)) which might have otherwise tried to employ the chiral reagent methods as proposed herein.

Therefore, as a prelude to attempting to deploy asymmetric, α-substituted benzylamine compounds as practical chiral auxiliary synthetic reagents in specific settings, it was decided to experimentally define the general scope and limits for subsequent removal of the α-substituted benzyl portion as impacted by the presence of the inherent, increase in steric bulk. Toward this end, the specific series of tertiary amine steric probes as shown within Table 1 was first synthesized. These compounds specifically model the steric environment for intermediates which will need to undergo debenzylation smoothly in order to successfully use the proposed reagents in any practical manner. By intention, the probes span a considerable range of the perceived steric impediment.

TABLE 1

Structures of molecules synthesized to probe the steric impediment toward N-debenzylation that results from employing asymmetric versions of a simple benzyl-group.

$$R_3 - \underset{\underset{Ph}{|}}{\overset{\overset{NR_1R_2}{|}}{C}} - H$$

| Name | $R_1$ | $R_2$ | $R_3$ |
|---|---|---|---|
| N,N-dipropyl-benzylamine (1) | propyl | propyl | H |
| N-isopropyl-N-propyl-benzylamine (2) | propyl | isopropyl | H |
| N,N-diisopropyl-benzylamine (3) | isopropyl | isopropyl | H |
| N,N-dipropyl-α-methylbenzylamine (4) | propyl (α) | propyl (α) | $CH_3$ |
| N-isopropyl-N-propyl-α-methylbenzylamine (5) | propyl (α) | isopropyl (α) | $CH_3$ |
| N,N-diisopropyl-α-methylbenzylamine (6) | isopropyl (α) | isopropyl (α) | $CH_3$ |

It was found upon careful examination of their N-debenzylation rate profiles, that this reaction is not impeded in any predictable manner that is proportional to increasing steric bulk. In fact, the most sterically hindered system, 6 was found to exhibit the fastest rate of N-debenzylation. These results are summarized in Table 2. A detailed description of these studies can be found in a recent M.S. degree thesis submitted to the University of Toledo (Y. Ni, Synthesis And N-Debenzylation Of Steric Probes To Define The Practical Limit For Employing Poten tial Benzylamine-Related Chiral Auxiliary Reagents) that is hereby incorporated in total by its reference herein.

TABLE 2

Comparison of the reaction rate data as measured by high pressure liquid chromotographic (HPLC) assay, to the steric features for 1 to 6: (a) Reaction time is defined as the time needed for at least 95% completion of the hydrogenolysis reaction. (b) Reaction rate is defined as moles substrate reacted per minute from T = 0 to 80% conversion and is reported as mean ± sd. © The steric energy values were obtained through CS Chem3D Pro. (d) Molar refractivity values were obtained using standard algebraic methods from literature tabulated data.

| Probe molecule | Reaction time (min) (a) | Reaction rate (mole/min) (b) | Steric energy (kcal/mole) (c) | Steric Molar refractivity (d) |
|---|---|---|---|---|
| 1 | 80 | $(3.81 \pm 0.16) \times 10^{-4}$ | 9 | 0 |
| 2 | 120 | $(2.20 \pm 0.13) \times 10^{-4}$ | 12 | 5 |
| 3 | 360 | $(9.57 \pm 0.34) \times 10^{-5}$ | 15 | 9 |
| 4 | 180 | $(1.84 \pm 0.06) \times 10^{-4}$ | 13 | 5 |
| 5 | 100 | $(2.80 \pm 0.11) \times 10^{-4}$ | 16 | 9 |
| 6 | 20 | $(1.46 \pm 0.01) \times 10^{-3}$ | 25 | 14 |

These completely unexpected results clearly show that the heretofore prevailing dogma about steric features limiting the potential use of such reagents in the proposed manner is actually not applicable. Interestingly, this appears to be the case even within the most extreme of such steric environments envissioned for the reagent's potential ussage, i.e. in compound 6 where all three positions α- to the nitrogen atom have been additionally substituted. Instead, these results indicate that when the net steric features are relatively small, subtle increments of steric bulk do impede the reaction rate. However, when the overall steric features are relatively large and a significant component is specifically located on the benzyl methylene carbon (i.e. the same α-position within the reagents which will be utilized to achieve the chirality for delivery by the methods proposed herein), further increments of steric bulk actually result in a faster reaction rate. Apparently, two opposing factors are manifest simultaneously at the level of the reaction mechanism. One is that the presence of steric bulk can interfere with the discrete process whereby hydrogen enters the reactive site of a given substrate such that this factor tends to slow the reaction. The other factor is that steric bulk can increase the net strain energy of the specific nitrogen-carbon bond to be broken and thus render it more susceptible to the reaction. Importantly, since all of the model reactions proceeded smoothly under reasonably mild reaction conditions, the studies clearly demonstrate that α-substituted benzylamines can indeed be deployed as chiral auxiliary reagents and that α-substituents even larger than a simple methyl group can be expected to be tolerated during N-debenzylation in any given instance. This completely unexpected finding, then, provides the confidence needed to deploy the method toward eventual use in a practical manner and constitutes the main factor of the inventive aspect of this disclosure.

SUMMARY OF THE INVENTION

Briefly, the present invention provides methods of deploying a family of chiral benzylamine-related reagents illustrated below by 7 during chemical syntheses in an auxiliary manner whereby the chiral benzyl portion of the reagent, as illustrated by 8, is subsequently removed in a separate and convenient step that renders the overall process suitable for use in process and larger-scale, manufacturing type chemical manipulations.

R=Substituent that is to be present in final compound or H (which can eventually be converted to a desired substituent); *=Asymmetric atom present as either pure S or pure R but not as the S.R racemic mixture; Ø=Unsubstituted phenyl; para-methoxyphenyl or ortho, para-dimethoxyphenyl; R'=Variety of polar, non-polar, bulky and non-bulky groups: Me, i-propyl, t-butyl, $CO_2Me$, $CO_2$i-propyl, $CO_2$ t-butyl, —$CO_2H$ and OH: n=0, 1 to 5 with the proviso that when R'=OH, n must be at least 1; and n'=1 or 2 (H absent) and when 2, Ø and R' need not be the same in both instances and the special circumstance presents itself that in one of the two occurrences, both R' and n can be completely absent, i.e. one of the two auxiliaries then reducing to the simple unsubstituted benzyl case.

Furthermore, in addition to delivering a nitrogen atom which is either substituted or unsubstituted (R=H) during the initial reaction of the overall synthetic process, the asymmetric nature of the benzyl group is used to bestow an assymetric bias toward formation, separation or subsequent reactions of the diastereomeric intermediates that result from reaction of the reagents with the racemic modifications of substrates which also possess one or more asymmetric centers. Schemes 4 and 5 illustrate the general method of the invention in a summarial fashion. They are not meant, however, to limit the overall scope for the deployment of these reagents.

Stereoselective production of asymmetric amines using α-substituted benzylamine systems as chiral auxiliary synthetic reagents: 9 is a racemic substrate (sub) which has at least one asymmetric center in addition to an electrophilic center (X): 7 is an optically pure chiral (*) auxiliary reagent wherein R' is a substituent having selected physical properties such as specified elements of steric bulk, and R is either a group that is desired in the final product or is H which can be subsequently substituted by a group desired to be present in the final product during any point in the synthesis but most preferably prior to *Step 3*; 10 and 11 are diastereomeric tertiary or secondary amine intermediates which are mixtures or are separated single diastereomers, respectively; and 12 is the desired optically pure amine product. Furthermore, R' can be a variety of bulky and non-bulky, polar and non-polar groups which are further specified by an emphasis upon their ease/cost of preparation for ultimate use as inexpensive chiral reagents in process chemistry. The closely related Di-N-substituted dibenzylamine systems (i.e. tertiary amine versions of 7 where n' = 2 and which are not specifically depicted above) will form quaternary ammonium intermediates after Step 1 in this scheme and these can then be di-debenzylated to yield the same product 12. *Step 1* represents any of the various N-substitution methods; *Step 2* represents a fractional recrystallization or chromatographic separation when necessary or convenient; and *Step 3* represents a catalytic hydrogenolysis ('debenzylation') reaction or other convenient method of removing benzyl groups.

9

-continued
Exemplary tracking of the stereochemical elements for the three types of stereochemical interactions that can occur during Step 1. In all of these examples, a 2-fold excess of the racemic substrate 9 is combined with one equivalent of the stereochemically pure enantiomeric reagent 7. A) Use of (S)-Reagent where no stereochemical bias is obtained, i.e. Path a is observed. B) Use of (S)-Reagent where a significant stereochemical bias is obtained for the preferential production of (S), (S)-diastereomeric intermediate 11-I, i.e. Path b is observed. Also note that in this case, unreacted 9 also becomes enriched with its opposite enantiomer (R) such that 9' is now stereochemically enhanced for a separate reaction using the (R)-Reag form that can then very favorably produce the (R), (R)-Sub-Reag intermediate in preference over the diastereomeric (S), (R)-Sub-Reag intermediate. C) Use of (R)-Reagent where no stereochemical bias is obtained. Note that this possibility is redundant to and in stereochemical accord with possibility A. D) Use of (R)-Reagent where a significant stereochemical bias is obtained for the (S), (R)-diastereomeric intermediate 11-III, i.e. Path b' is observed. Also note that in this case, unreacted 9 also becomes enriched with its opposite enantiomer (R) such that 9' is now stereochemically enhanced for a separate reaction using the (S)-Reag form that can then very favorably produce the (R), (S)-Sub-Reag intermediate in preference over the diastereomeric (S), (S)-Sub-Reag intermediate. Neither D nor its second, separate reaction are stereochemically redundant to possibility B and its second separate reaction. Alternatively, the last two possibilities where racemic substrate is reacted with the (S)-Reagent to preferably provide the (R), (S)-diastereomeric or with the (R)-Reagent to preferably provide the (R), (R)-diastereomer are indeed stereochemically redundant to possibilities D and B, respectively. Finally, 11-I and 11-IV represent enantiomers which will have identical physicochemical properties unless exposed to another asymmetric element. 11-II and 11-III are also enantiomeric. All other relationships are diastereomeric such that differences in physicochemical properties can be expected between these intermediates until the chiral auxiliary portion is subsequently removed.

Based upon literature precedent such as that disclosed by Scheme 2, it is reasonable to anticipate that during Step 1, racemic substrate 9 can sometimes combine with optically pure reagent 7 to preferentially provide a majority of one over the other of the two possible diastereomers directly (Path b). However, even when no asymmetric bias is observed during Step 1 (Path a), the two diastereomer products present as intermediate 10 will differ in physical properties such as solubility, chromatographic behavior, boiling point or melting point. Thus, as is well-established within the art and as is specifically disclosed by Scheme 1, the desired single diastereomer 11 may be able to be conveniently separated under a variety of selected conditions such as recrystallization or chromatography during the workup (Step 2) of the first reaction. Finally, based upon the precedent disclosed by Scheme 3, it is also possible to effect an asymmetric cleavage during Step 3 whenever the chiral auxiliary in one or the other of the diastereomeric amines lends itself to preferential removal by hydrogenolysis. That the latter reaction can be made to occur at all under reasonably mild chemical conditions suitable for scaled-up, process chemistry manipulations has now been clearly shown to be the case by the totally unexpected results of the aforementioned experiments described herein and futher disclosed within Tables 1 and 2.

It is the overall method of being able to generally deploy reagents 7 within the summarial framework of Scheme 4 which is broadly contemplated within the present invention. It will be appreciated that this is because of our completely unanticipated findings that the benzyl-related portions of such reagents will indeed be able to be readily removed.

BRIEF DESCRIPTION OF THE FIGURES

The invention consists of the method for using reagents and key synthetic steps in the various arrangements, combinations and improvements as shown and described herein. The accompanying figures, which are incorporated in and constitute a part of the specification, illustrate certain embodiments of the invention and together with the description help to convey how to use the invention. These figures, however, are not meant to narrow the overall scope of the invention. Of the figures.

DETAILED DESCRIPTION OF THE INVENTION

By using the method of this invention, the RNH portion within reagent 7 is delivered to a racemic substrate and the product ultimately formed by the process becomes significantly enhanced toward one of its enantiomers, if not completed separated into only one of its two possible enantiomers. The specific asymmetric separation aspect is based upon the diastereomeric interactions afforded by the auxiliary portion of the reagent illustrated within portion 8 of 7 wherein the entire portion 8 is then subsequently removed as a distinct step. The latter can be undertaken at any later and convenient point within an overall synthetic pathway leading to a desired target molecule. Indeed, it may actually be advantageous to delay the removal of 8 so as to further utilize this moiety as a classical protecting group for the amine functionality during other synthetic steps which may also need to be undertaken along the overall synthetic pathway eventually leading to a desired target molecule.

While R can be either a substituent or H in 7, R is preferable not H within 12 because of the greater ease for conducting Step 3 when going from a tertiary amine to a secondary amine, as has been disclosed by the prior art conveyed herein within the background section (e.g. secondary<tertiary). The specific composition of R will be dictated by what the R group will be in any given target molecule but it will generally include: alkyl from 1 to 10 carbons; aryl; aralkyl of from 6 to 20 carbons; or functionalized versions of alkyl, aryl and aralkyl providing that said functional groups are not basic amines and when said groups are hydroxy and carboxy or other reactive functionalities, they are also protected in a manner that is commonly practiced within the synthetic art so as to make these groups themselves non-reactive during the key Steps 1, 2 and 3 in Scheme 4.

While the asymmetric carbon designated by an asterisk in 7 must be present as only one of its two enantiomeric possibilities, i.e. either as pure (R) or pure (S) and not as racemic (R, S), both of the pure-enantiomer possibilities are contemplated for use in the present invention. This is because as demonstrated by the possibilities shown in Scheme 5, the distinct enantiomeric form of each reagent that is needed to produce the desired enantiomeric product will vary in a unique manner according to each individual application of the overall method. Thus, the preferred enantiomer for using these reagents must be determined experimentally during the course of their use according to Scheme 4 in each distinct application.

The Ø is used herein to designate both a phenyl ring and a substituted phenyl ring, such as para-methoxy or (ortho-, para)-dimethoxy. The simple unsubstituted case or the para-methoxy case would, however, be generally preferred for use during debenzylation (Step 3) by catalytic hydrogenolysis. The (ortho-para)-dimethoxy case is preferred only when other means of debenzylation (e.g. treatment with $K_2S_2O_8$) must be undertaken as an alternative to debenzylation, for example when there are other positons within the substrate that are also susceptible to hydrogenation conditions.

The various compositions possible for R' are intended to cover a range of steric and lipophilic/polar properties among the possible groups in order to form a family of these reagents that, in turn, encompasses a range of chemicophysical properties such that the latter can be rationally or combinatorially traversed experimentally in order to optimize the stereochemical bias desired for each distinct application of the overall method. Specifically, R' can be: alkyl of from 1 to 10 carbons; aralkyl of from 6 to 20 carbons; various carboxylic esters preferentially having branched chain alkyl adducts in order to enhance their stability toward hydrolysis; carboxy; hydroxy; and finally, nitrogen containing systems provided that such systems are not basic.

The length of n varies according to the nature of the R' group with: 0 being preferred for R'=alkyl and aralkyl; 0 to 5 being possible for all other modifications of R' with the proviso that in cases when R'=OH, or non-basic nitrogen systems, n must be at least 1. During applications of the overall method, although not rigorous in this specification, it is contemplated that lower values for n (i.e. 0, 1, 2) may be more useful when the racemic asymmetric center present in the substrate molecule is located near (i.e. alpha-, beta- or gamma) the point where the nitrogen will be inserted while higher values or n (i.e. 3, 4, 5) may be more useful when the racemic asymmetric center present in the substrate molecule is located more distant (i.e. greater than gamma-) from the point where he nitrogen will be inserted.

The value of n' can be either 1 or 2 providing that when n'=2, the second occurrence replaces the H as depicted on the nitrogen in 7. Most preferably, n' will be 1 for most applications of the method. However, when crystallization of the diastereomeric intermediate 10 is particularly regarded as an advantageous way to effect purification or stereochemical enhancement, then the case where R is a substituent (R not H) and n'=2 becomes at least equally preferable to the n'=1 case because such reagents will very conveniently provide quaternary ammonium salts when conducting Step 1. The latter types of compounds as a broad class are well known within the art for their enhanced crystalline properties when compared to their related families of tertiary and secondary amine salts. Furthermore, the propensity for benzylated quaternary ammonium systems to undergo debenzylation reactions is generally as favorable if not faster than that for their tertiary amines counterparts. Finally, when n'=2, the two occurrences need not be the same and the special circumstance presents itself wherein for one of the two occurrences both R' and n can be completely absent, i.e. one of the two auxiliaries then reducing to the simple unsubstituted benzyl case.

For all of the above, alkyl is taken to encompass straight-chain, branched and cyclic occurrences within the range of carbon numbers specified in each case. Aryl is taken to mean both unsaturated hydrocarbon systems and the common heterocyclic systems such as pyran, furan and pyridine.

Some of the simpler structural members of the overall family of reagents represented by 7 are directly available from commercial sources and are already in the form of their pure enantiomeric isomers, namely many of those wherein R=H and n'=1 such as (α-methylbenzylamine (n=0, R'=CH₃), α-aminophenylacetic acid also known as α-phenylglycine (n=0, R'=CO₂H) along with its methyl ester (n=0, R'=CO₂Me), and α-amino-α-phenylethanol also known as α-phenylglycinol (n=1, R'=OH). The remainder of the reagents where R=H and n'=1, are either compounds already known within the literature or are compounds which can be readily prepared via standard, analogous literature methods, either as their pure enantiomers or as their racemic mixtures followed by the use of classical resolution techniques or asymmetric column chromatography to obtain the enantiomeric forms. For example, Scheme 6 illustrates one convenient synthetic route which can provide for ready access to a variety of the members within 7 where n'=1 as the hydrochloride salts of their racemic mixtures.

Scheme 6
Literature-based pathway for ready synthesis of a variety of racemic α-substituted benzylamines.

Alternatively, when R is a substituent other than H, only a very few of the family members are already known within the literature as either of their pure optical isomers, the case of (R)-N-isopropyl-α-methylbenzylamine (R=CH(CH₃)₂; n=0; R'=CH₃; and n'=1) being one notable example. However, all of these family members are again obtainable by employing standard synthetic and separation techniques which are well known within the art. For example, free amine versions of the products from Scheme 6 can be further reacted with various R containing starting materials according to the considerable and well established common art for N-alkylation reactions, e.g. Scheme 7. Finally, the same situation applies to the obtainment of the remaining family members wherein n'=2 and where extensive literature searching suggests that essentially all of these species represent novel compositions of matter. Thus, the entire family of reagents encompassed by 7 includes some commercially available species, some compounds known to the art, and finally, several compositions which appear to be novel. While the present invention fully relates to the method of using all of the species within this closely-related family of reagents as specified above, it should not be construed to further preclude other patents by any parties pertaining to the development of specific synthetic methodologies which lead to the production of the novel compositions of matter which also happen to be encompassed within 7. Several specific examples of the family members are illustrated below. The purified forms of both enantiomers are meant to be included as part of each structure even though the specific stereochemistries are not displayed. These examples are not intended to limit the scope of the overall family membership.

-continued

Since the total number of variables which can be optimized for the three key steps in any specific application of the overall method is extremely large, the following descriptions for each of the steps are meant to convey how to practice and quickly adopt the overall method by first illustrating how the steps can be generally conducted by anology to well established chemical scenarios. A specific application is offered later as well. For the following, the indicated specifications are not intended to limit the scope of utility for the overall method since part of the method's virtue lies in its very general utility and wide variety of applicatons within the field of asymmetric synthetic chemistry.

Step 1 can be conducted by any of the wide variety of common N-alkylation or N-aclyation-reduction schemes that are well established within the chemical literature. A brief review of several of these types of reactions is contained in the aforementioned paper by P. Erhardt (Synth. Comm., 13, 103 (1983)) all of whose contents and references are hereby incorporated by reference. This article also reviews the merits of employing benzyl containing systems as part of sterically hindered reagents which can be used in a very practical manner to control the regiochemistry or degree of alkylation during these types of reactions. Thus, it is noteworthy that the present invention provides an overall method which can simultaneously deliver a nitrogen atom during synthesis while controlling both the regiochemistry and a specifically desired stereochemical consequence from asymmetric substrates by taking advantage of very practical chemical manipulations which are amenable to scaled-up process chemistry and chemical manufacturing procedures.

Some of the more preferred means of accomplishing Step 1 within the overall method include the use of the common reactions shown by the following Scheme 7. Note, however, that the tertiary amine versions of the reagents (R=substituent; n'=2) are limited to the classical N-quaternization type reactions, e.g. reaction with alkyl halides or with other systems bearing a good leaving group (LG).

Practical chemical procedures which can be readily employed to initially combine racemic substrates with the chiral auxiliary synthetic reagents as depicted in *Step 1* <u>Scheme 4</u>. LG = Leaving Group such as halide. R" = H or alkyl.

The prefered conditions for conducting Step 1 other than for the special case of using an aqueous NaOH/dioxane system when dealing specifically with the carboxylic acid containing reagents, involve refluxing the reactants in a common organic solvent, typically an alcohol such as methanol or ethanol, for a period of at lest a few hours to at most a few days, with either an organic base present to capture a leaving group if one is so produced or an organic acid present to catalyze a reduction when the latter is simultaneously effected by the additional presence of a hydride reagent, such as $NaBH_4$ or $NaCNBH_3$. referred organic bases include pyridine or triethylamine which are typically used in an amount equimolar to the chiral auxiliary reagent. Preferred acids include acetic acid which is typically used in amounts needed to maintain a pH of about 3.0–6.0 during reactions involving hydride reductions. Importantly, the racemic substrates are typically utilized in at least a two-fold molar excess over the chiral auxiliary reagent unless the latter's stereochemical preference for reaction with only one of the two substrate enantiomers is so dramatic and is so exquisitely selective in a given instance that the reagent simply does not react at all with the other substrate isomer. Furthermore, it may still be advantageous to employ a 2:1 substrate:reagent ratio even in this ideal setting in order to consume all of the amine-containing reagent so as to make the separation of the amine-containing product from unreacted starting materials an easier task, in this case the unreacted starting materials then being only an excess of the non-amine containing substrate material, as was shown within Scheme 5. Additionally, when the asymmetric preference for one enantiomer within the substrate is low, it may become advantageous to employ a considerably larger excess of the substrate material, such excesses possibly becoming as high as a 20:1 ratio of substrate:chiral auxiliary reagent. During larger-scale applications, this larger ratio strategy may still be practically useful when the unreacted substrate can be readily recovered or directly recycled in an on-line process so as to be reused in additional, subsequent reactions upon receiving a new charge of the same chiral auxiliary reagent. The distortions that can occur in the racemic content of the substrate during Step 1 and the various ways that these possibilities can potentially be put to further advantage are shown in Scheme 5.

Step 2 is utilized in those cases where stereoselectivity during Step 1 is low. By virtue of the chiral auxiliary reagents specified herein, diastereomers are already formed at this point of the scheme such that the differences in physicochemical properties typically observed for diastereomers can be exploited directly to conveniently accomplish their separation. As indicated earlier, the quaternary ammonium versions of the reagent-substrate product will, in particular, exhibit preferred properties toward effecting separation by classical crystallization methods. The latter is then analogous to the huge body of well known chemical art whereby resolution is effected by formation of diastereomeric salts. Likewise, the tertiary amine and secondary amine versions of the reagent-substrate products, again already diastereomeric from Step 1, can also be subjected to classical resolution via crystallization techniques by simply forming convenient and well-behaving salts from the much larger array of non-asymmetric inorganic and organic acid possibilities, HCl and oxalic acid exemplifying just two of such preferred salt forming species. Alternatively, the secondary and tertiary free amine versions are suitable for standard (non-asymmetric) column chromatographic separation of their diastereomeric forms. This unique situation results specifically from the use of the chiral auxiliary reagents as deployed herein and it is notably distinct from the art since the classical formation of diastereomeric salts precludes the use of standard column chromatographic techniques. Previously, without the novel method as specified herein, either asymmetric column chromatography or further diastereomeric derivatizations would first have to be done on the intermediates. Thus, preferred column procedures for the separtation of intermediates 10 can take advantage of low cost column adsorbents such as silica gel with the use of common organic solvents for elution.

Step 3 constitutes removal of the chiral auxiliary portion of the reagent, represented by structure 8. Because of the aforementioned novel findings, this step can be conveniently accomplished with confidence under standard catalytic hydrogenation conditions which are well established within the chemical art based upon their considerable former use on less sterically hindered and non-asymmetric, simple benzylamine containing systems. Preferred conditions for this step involve dissolving the quaternary ammonium-type intermediates or tertiary amine-acid salt intermediates in an organic solvent such as methanol which also contains a catalytic amount of 10–20% Pd on activated carbon and hen hydrogenating the solution at room temperature under an atmosphere of 5–50 psi for a period ranging form several minutes to a few days. Secondary amine-acid salts can also be debenzylated in this manner but these will typically require longer reaction times and/or elevated temperature, the latter conditions generally being less suitable for larger-scale process chemistry and chemical manufacturing procedures. Additionally, since the starting materials for Step 3 are diastereomeric, Step 3 may also be examined in each unique case for its potential to preferably debenzylate only one of the two diasteriomeric isomers. However, stereoselective success in this situation would then produce, for example, one product enantiomer as a secondary amine and the other diastereomeric substrate remaining as a tertiary amine. A separation of these two amine-containing species would then still have to be effected. Therefore, this approach toward accomplishing a stereoselective separation is preferable only for those cases which also happen to lend themselves for ready isolation of only the product as its single enantiomer over the other diastereomeric starting material component.

With the aforementioned specifications drawn from well-established chemical situations serving as a background, the following description specifically conveys an overall strategy for approaching a given, new chemical entity: 1) Design entire synthetic route to afford as much flexibility as possible for insertion of the chiral auxiliary synthetic reagent, for example by as many of the reactions depicted in Scheme 7 as possible; 2) Taking at least an alkyl version, a hydroxy-version and a carboxylic ester version as representatives of the reagent family 7, conduct Step 1 using a two-fold excess of each of the sub-X versions which were conveniently afforded by 1) while exploring several common solvents ranging in different polarities (temperature should be constant for all reaction systems within a given sub-x:reagent pair experiment and duration should proceed until the reagent component is either completely utilized or until several days have elapsed); 3) Assay crude products for stereochemical preference using, for example, their diasteriomeric difference evidenced by HPLC or NMR spectroscopy; 4) Conduct purification of these intermediates employing only preliminary attempts to separate diastereomers (Step 2 options) so as to uncover just those relationships which readily and dramatically lend themselves to diastereomeric separations; 5) Effect debenzylation reactions according to the specifications which were elaborated for Step 3 and assess stereochemical nature of reaction at crude product stage; 6) Taking all of the experiments 2) to 5) into account, determine which of Steps 1 to 3 is the best one to focus more detailed studies upon. In general, it is anticipated that Step 1 will be the easiest place for separating the desired product from other materials provided that stereochemical preferences have been obtained at this point.

The following working example is also provided to further demonstrate how to deploy the present invention within the context of a specific application. It is, however, not intended to limit the scope of the invention. Target molecule 13 represents the prototypical structure for a typical β-adrenergic receptor blocking agent. These types of compounds are among the world's most widely utilized pharmaceuticals and are commonly prescribed for the treatment of hypertension, angina pectoris and cardiac arrhythmias (P. Deedwania, *Beta-blockers and Cardiac Arrhythmias,* Marcel Dekker, Inc. (1992)). Most of the β-blockers are 1-(alkylamino)-3-(aryloxy)propan-2-ols where the aryl moiety can be one of a large variety of aromatic groups with or without further substituents, and the secondary N-alkyl moiety is typically an isopropyl or a tertiary butyl group, although other substituents on the nitrogen can occur as well.

13

It is well known that the (R)- and (S)-enantiomers of these compounds possess very different β-blocking activity, (S)-enantiomers typically displaying nearly 100 times higher β-blocking potency compared to their (R)-enantiomers (ibid.). Nevertheless, many of the world's β-blockers are still sold as racemates. For example, propranolol (K Stoschitzky, et al. *Naunyn-Schmiedeberg's Arch Pharmacol.,* 339, 474 (1989)), atenolol (K. Stoschitzky, *Chirality,* 5, 15 (1993)) and carvedilol (R. Ruffoolo, et al., *Eur. J. Clin. Pharmacol.,* 38, S82 (1990)) are all marketed as their racemic mixtures.

As mentioned in the background section, the recent trend toward using single stereoisomer pharmaceutical agents has likewise stimulated a search for practical methods to specifically prepare β-blockers in optically active form. Toward such an end, several different approaches have been examined such as the use of classical, fractional crystallization of diastereomeric salts (B. Wasson et al., *J. Med. Chem.,* 15, 651 (1972)), direct and indirect chromatography-based separations (J. Jurczak et al., *Tetrahedron,* 42, 447 (1986); L. Fisher et al. *J. Am. Chem. Soc.,* 113, 9358 (1991); H. Aboul-enein and M. Islam., *J. Chromatogr.,* 511, 109 (1990); C. Davis, *J. Chromatogr.,* 531, 131 (1990)), asymmetric reagents and catalysts (H. Sasai et al., *Tetrahedron Lett.,* 34, 855 (1993); H. Bevinakhi and A. Banerji, *J. Org. Chem.,* 56, 5372 (1991); H. Takahashi et al., *J. Am. Chem. Soc.,* 112, 5876 (1990); J. Klunder, et al.,*J. Org. Chem.,* 51, 3710 (1986); S. Miyano, et al., *J. Org. Chem.* 50, 4350 (1985); T. Katsuki, *Tetrahedron Lett.,* 25, 2821 (1984); J. Backvall et al., *Tetrahedron Lett.,* 23, 943 (1982)), chiral building blocks (E. Warmerdam et al., *Helv. Chim. Acta,* 77, 252 (1994); M. Bouzoubaa et al., *J. Med. Chem.,* 28, 896 (1985); J. Klunder et al.,*J. Org. Chem.,* 54, 1295 (1989); Y. Tsuda et al., *Chem. Phar. Bull.,* 29, 3593 (1981); L. Weinstock et al., *J. Org. Chem.,* 41, 3121 (1976)) and use of specific asymmetric enzymatic reactions (T. Mitsuhiro and N. Akutsu. *Tetradedron, Asym.,* 3, 1381 (1992); Y. Wang et al., *Tetrahedron Lett.,* 30, 1917 (1989); Y. Terao et al., *Tetrahedron Lett.,* 29, 5173 (1988); N. Matsuo and N. Ohno, *Tetrahedron Lett.,* 26, 5533 (1985); S. Hamaguchi et al., *Agric. Biol. Chem.,* 48, 2055 (1984); S. Iriuchijima et al., *Agric. Biol. Chem.,* 46, 1593 (1982); S. Iriuchijima and N. Kojima, *Agric. Biol. Chem.,* 46, 1153 (1982)). All of these methods have advantages and limitations. While classical resolution is widely used industrially, successful applications are generally derived only after a tedious process of cumbersome experimentation (P. Newman, *Optical Resolution Information Center,* Vol. 1 (1978)). In addition, molecules devoid of functionality suitable for the formation of diastereomeric salts can present difficulties (*Chirality in Industry.* A. Collins. John Wiley & Sons (1992)). Synthetic methodology using chiral building blocks is limited by the availability or expense of the chiral pools. The asymmetric synthetic approach using chemical catalysis is still a relatively new field and has, so far, been limited by the general development of new catalysts, expense of the catalysts and scale-up problems (A Rao et al., *Tetrahedron, Asym.* 1, 697

(1988)). The biological methods have their advantages in specificity, safety and mild conditions, but are limited by the low volumetric productivity, the need for expensive cofactors, chemical and thermal instability, and incompatibility with organic solvents.

As can be seen in 13, the asymmetric atom in this class of compounds is located beta- to a secondary amine. Thus, an attractive alternative solution to the practical synthesis of optically pure β-blockers could utilize the novel α-substituted benzylamine chiral synthetic method as has been delineated herein.

In selecting a specific case within this class of compounds, I decided to consider this approach toward the preparation of (S)-esmolol which is shown as compound Scheme 8.

Scheme 8
Racemic, 14, and (S)-esmolol, 15.

Racemic esmolol was developed in 1982 (P. Erhardt et al., *J. Med. Chem.*, 25, 1402 (1982); P. Erhardt et al., *J. Med. Chem.*, 25, 1408 (1982)) and has been widely used for its special properties as an ultra short-acting β-blocker. Clinical studies have demonstrated an infrequent but annoying side effect involving irritation at the site of the infusion caused by the high concentration of the drug which is formulated as its hydrochloric acid salt (P. Turlapaty et al., *Am. Heart J.*, 114, 866 (1987)). However, since only the (S)-enantiomer is responsible for the desired biological properties (A. Barrett and V. Cullum. *Br. J. Pharmac.*, 34, 43 (1968)), the drug-acid salt concentration can be reduced by one-half without any loss in potency when only the (S)-enantiomer is present in the formulation.

In this case, the intended asymmetric synthetic approach can make use of the specific chiral α-substituted benzylamine reagent shown exactly in Scheme 9 (Step 1 of the third reaction arrow). This scheme is analogous to a well established manufacturing route for producing racemic esmolol where isopropylamine is used at this point to directly produce the final product. As mentioned before, it is reasonable to expect that racemic intermediate 16 can combine with an optically pure benzylamine derivative to preferentially provide one or the other of the two potential diastereomers. Alternatively, even if produced in equal amounts, separation could be effected at this point due to the diastereomeric nature of the two products. Finally, our unexpected findings demonstrate that the chiral auxiliary when so present in 17 can be confidently expected to be conveniently removable by hydrogenolysis, and while so doing, this step can afford yet another point for an asymmetric bias.

Asymmetric synthetic approach toward (S)-esomol using enantiometric N-isopropyl-α-methylbenzylamine as a chiral auxiliary syntheic reagent. This approach is analogous to the manufacturing route for producing racemic esomol which instead utilizes excess isopropylamine in Step 1 to directly produce the final product.

Optically pure α-methylbenzylamine is available from commercial vendors. It can also be obtained rather inexpensively since its racemic form has been shown to be readily resolved with tartaric acid (A. Cope, W. Moore, et al. *J. Am. Chem. Soc.*, 1243 (1970)). Formation of the requisite N-isopropyl derivative can be accomplished by a variety of standard N-alkylation methods. Likewise, the other starting material, racemic methyl 3-[4-(1,2-epoxypropoxy)phenyl] propionate, 16, can be readily prepared in two steps from commercially available material 3-[4-hydroxyphenyl] propionic acid. Nevertheless, to further expedite the deployment of the novel method while also continuing to emphasize the present context of providing an instructional example, close chemical model systems can also be conveniently adopted at this point which will allow both an even easier access to accessible starting materials and to the produciton of key standard compounds and intermediates. The latter can help to better display the overall technology even though they do not necessarily have to be prepared during the envisioned routine use of the novel method. Alternatively, it can be noted that the use of appropriate model chemistry can be a wise strategy in itself whenever the materials for a particular application are regarded as being either very expensive, precious or time-consuming for the reiteration phase during both initial deployment and continued optimization of the novel methodology. Thus, to expeditiously define the conditions which can optimize the stereochemical specificity for using the inventive method within the specific problem of the aforementioned β-blocker-related chemistry, the close model reactions and chemical manipulations shown in Scheme 10 were undertaken first. The precise experimental details for both the general β-blocker model chemistry and the specific case of esmolol are provided in the following list of specific Examples. Note that Examples 3 6, 7 and 14 do not necessarily need to be accomplished while deploying the novel method. Their inclusion within the present disclosure is for the purpose of providing easier chemical clarity within the overall context of better conveying the example cases.

0.78 g (98.7%) having appropriate NMR and IR spectra and a correct (±0.4%) elemental analysis for C, H and N: mp 160–161_C.

EXAMPLE 2

N-Debenzylation of N,N-Diisopropyl-α-methylbenzylamine

The amine picrate salt (2 mmole) from Example 1 was dissolved in water (10 ml) and the solution made alkaline (pH=11) by the addition of 40% KOH. The liberated free amine was extracted with ether (3×20 ml). The combined ether phases were dried and evaporated under reduced pressure to provide the free amine as a clear oil. The procedure was quantitative. TLC and NMR data were used Scheme 10

Expeditious dellineation of method conditions within the setting of classical β-blocker chemistry. For this first-pass analysis, the R' = CH$_3$ member of the reagent family was utilized.

EXAMPLE 1

Synthesis of N,N-Diisopropyl-αMethylbenzylamine For Use as an Extremely Hindered α-Substituted Benzylamine A mixture of 15 ml of diisopropylamine (107 mmole) and 3 ml of (1-bromoethyl)benzene (4.068 g, 22 mmole) was stirred and heated to reflux for 118 hours. Evaporation of most of the excess diisopropylamine provided an oily residue. Attempted crystallization of the residue from methanol:ether (1:1) gave a white suspension, which was filtered and rinsed with ether twice. Evaporation of the solvent from the filtrate and washings gave an oily, crude product (TLC $R_f$ 0.6 in ethyl acetate) which was further purified according to the following procedure: The oily residue which was taken up in 50 ml water with acidification to pH 5 (2N HCl) and washed by partitioning with ether (3×20 ml). The aqueous layer was then adjusted to pH 11 (40% KOH) and extracted with ether (5×20 ml). The collected ether phases were dried over anhydrous magnesium sulfate and evaporated under reduced pressure to provide 0.4 g (8%) of an oily product with an NMR spectrum appropriate for the desired material: bp 101–103_C. (1.5 mm Hg).

The free amine oil was also crystallized by formation of its picrate salt according to the following procedure: A solution of the free amine, 0.37 g (1.8 mmole) in ether (3 ml), was combined with a solution of nearly equimolar picric acid 0.7 g (2.0 mmole, 35% water) in ether (3 ml) to produce a yellow solid which was recrystallized from ethanol. The resulting light-yellow-colored crystals were washed with small amounts of cold ethanol and ether and then dried under vacuum to finally provide a yellow crystalline product to verify structural integrity. The free amine (2 mmole) was dissolved in methanolic HCl (20 ml prepared previously with HCl gas) assuring that the pH remained acidic (pH ca. 3). Evaporation of methanol gave the hydrochloride salt as a colorless thick oil. Trace amounts of solvent were removed under high vacuum. The procedure was quantitative with both TLC and NMR data being used to verify structural integrity.

250 mg of the hydrochloride salt was dissolved in 50 ml of methanol and shaken in a Parr Apparatus with 25 mg of 10% palladium on carbon under 30 psi hydrogen gas at room temperature. Samples (ca. 0.5 ml) for the kinetic studies were taken via syringe every 10 minutes. Hydrogen pressure was quickly reestablished after each sampling. By measuring both the loss of starting material and the formation of toluene according to a quantitative HPLC method it was determined that this reaction was essentially done (>95%) within 30 minutes. Purification of the product was accomplished by filtering the catalyst and evaporating the solvent under reduced pressure. Crystallization of N,N-diisoproylamine hydrochloride was then accomplished from methanol:ether (1:1) to provide material whose NMR spectrum was identical to that of an authentic sample: m.p. 217–219_C. [Lit. (Aldrich Catalog, 551 (1996–1997)) 216–218 C.].

EXAMPLE 3

Preparation of (S,R)-1-(Isopropyl)-3-phenoxy-2-propanol For Use as a Racemic Product Standard A solution of 1.51 gm (10 mmol) of racemic 1,2-epoxy-3-phenoxypropane in 25 ml (300 mmol) isopropylamine and 25 ml of methanol was heated to reflux for 4 hours. The reaction mixture was evaporated under reduced pressure to provide a white solid which was recrystallized from methanol:water (ca. 2:1) at room temperature. 1.64 gm (78%) of white crystals were obtained having an appropriate NMR spectrum: m.p. 96–99_C. Formation of a hydrochloride salt was accomplished by dissolving a 410 mg portion of the free amine in saturated methanolic HCl, assuring that the pH was retained at ca. 3, evaporation of this solution to a semi-solid and then recrystallization from methanol:ether (ca. 1:10) while at room temperature. 330 mg (69%) of white crystals were obtained having an appropriate NMR spectrum: m.p. 115–116_C. [Lit. (P. Erhardt et al., *Journal Medicinal Chem.*, 25 1402 (1982)) m.p. 112–114_C.].

EXAMPLE 4

Preparation of (S)-N-Isopropyl-α-methylbenzylamine For Use as a Chiral Auxiliary Synthetic Reagent A solution of 1.29 ml (10 mmol) (S)-α-methylbenzylamine, 1.42 ml (20 mmol) acetone and 0.628 gm (10 mmol) of sodium cyanoborohydride in 30 ml of methanol was cooled over a dry ice/acetone bath. Acetic acid (~0.6 ml) was added to adjust the pH to 6 and then the solution was allowed to gradually reach room temperature. After a total of 24 hours stirring, the methanol was removed by rotary evaporator. The residue was dissolved in 50 ml of 20% aqueous $Na_2CO_3$ and extracted four times with 20 ml of ethyl ether. The combined ether phases were dried over anhydrous $MgSO_4$ and then evaporated to provide 1.6 gm of a clear oil. The oil was chromatographed on a silical gel column employing ethyl acetate:ether (2:1) as the eluent. 1.4 gm (86%) of a clear oil was obtained having an appropriate NMR and $[\alpha]_D=-57\_(c=1, MeOH)$. Formation of a hydrochloride salt was accomplished by dissolving the free amine in saturated methanolic HCl, checking pH to insure acidic character (pH ~3), evaporation of this solution on a rotavap and then crystallization of the resulting amorphous solid from methanol:ether (~2:1) while at refrigerator temperature (~1–2_C.). 1.6 gm (80%) of white crystals were obtained having an appropriate NMR and correct elemental analysis (within ±0.4%) for C, H & N: m.p. 259–261_C.; $[\alpha]^{D25}=-23.6\_(c=1.6, MeOH)$ [Lit. (C. Cain et al., *Tetrahedron*, 46, 523 (1990)) for the (R)-enantiomer $[\alpha]_D^{25}=+22.5\_(c=2.03, EtOH)$].

EXAMPLE 5

Preparation of (R)-N-Isopropyl-α-methylbenzylamine For Use as a Chiral Auxiliary Synthetic Reagent This material was prepared in similar yield by a manner identical to that for Example 4 except that (R)-α-methylbenzylamine was utilized as the starting material. The NMR and elemental analysis were correct for the assigned structure: m.p. 260_C.; $[\alpha]_D^{25}=+23.0\_(c=1.6, MeOH)$ [Lit. (C. Cain et al., ibid) $[\alpha]_D^{25}=+22.5\_(c=2.03, EtOH)$.

EXAMPLE 6

Preparation of (S),(S)-2-Hydroxy-3-[[N-isopropyl-N-(α-methyl)benzyl]amino]propoxybenzene For Use as a Diastereomerically Enriched Intermediate Standard A solution of 0.19 gm (1.26 mmol) of commercially available (S)-1,2-epoxy-3-phenoxypropane and 0.245 gm (1.53 mmol) of (S)-N-isopropyl-α-methylbenzylamine in 5 ml of methanol was heated to reflux for 72 hours. The methanol was then removed by a rotovap to provide an oil which was further purified by silica gel column chromatography using methylene chloride:ethyl acetate:28% aqueous $NH_3$ (20:1:0.1) as the eluent. 0.318 gm (81%) of a clear oil was obtained having an appropriate NMR spectrum (FIG. 1): b.p. 153–155_C. (0.4 mm Hg); $[\alpha]_D^{25}=-16.1\_(c=0.55, MeOH)$.

EXAMPLE 7

Preparation of (R),(S)-2-Hydroxy-3-[[N-isopropyl-N-(α-methyl)benzyl]amino]propoxybenzene For Use as a Diastereomerically Enriched Intermediate Standard This material was prepared and purified in a manner identical to that for Example 6 except that the (R)-version of 1,2-epoxy-3-phenoxypropane was utilized as the starting material. 0.152 gm (63%) of a clear oil was obtained having an NMR appropriate for the assigned structure (FIG. 1): b.p. 178–181_C. (0.5 mm Hg); $[\alpha]_D^{25}=+24.5\_(c=0.56, MeOH)$.

EXAMPLE 8

Reaction of Racemic Epoxide Substrate With (S)-N-Isopropyl-α-Methylbenzylamine (Step 1)

Figure 2:
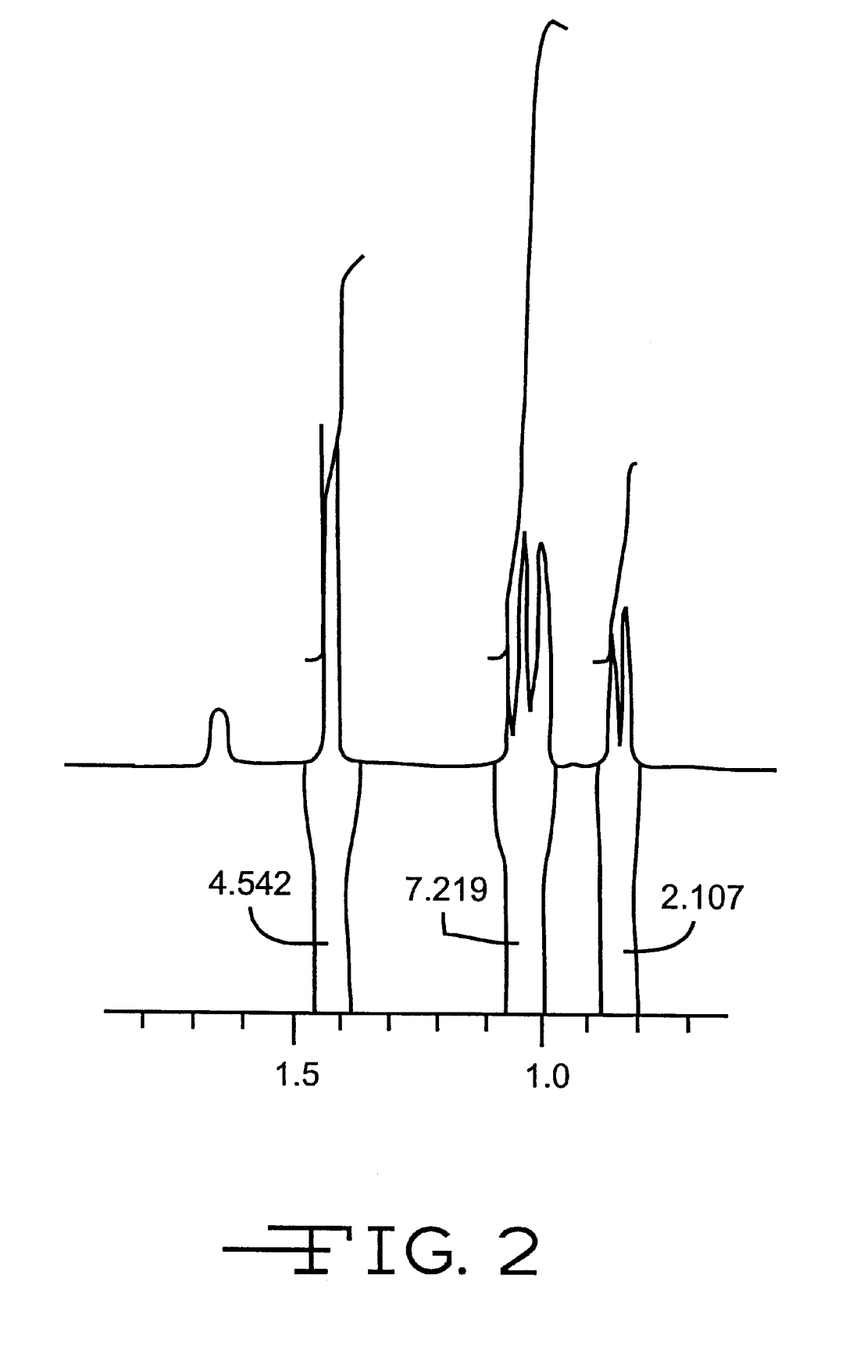
FIG. 2 displays the relevant region of the NMR spectra for the diastereomeric product mixture obtained after reaction of racemic model substrate material 9 with the chiral auxiliary reagent (S)-N-isoproyl-α-methylbenzylamine having conducted Step 1 in methanol and observed very little stereoselective enhancement during the reaction, i.e. diastereomerically mixed intermediate 10 case.
Figure 3:
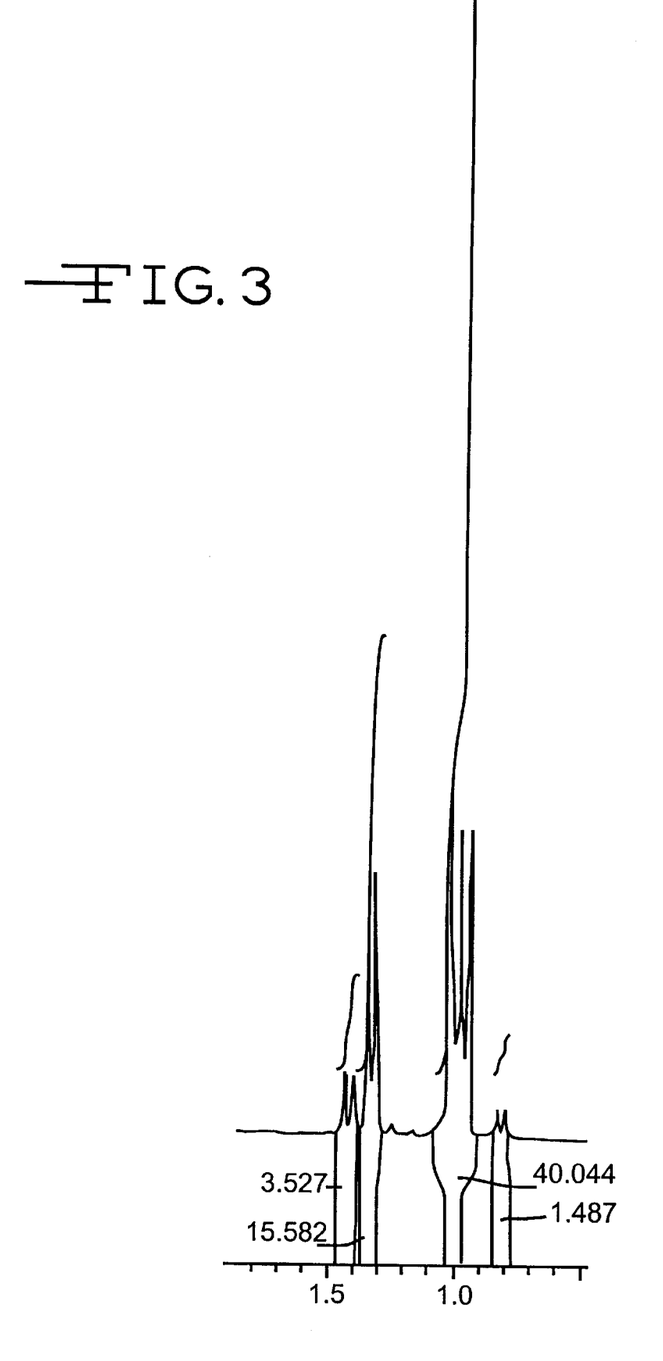
FIG. 3 displays the relevant region of the NMR spectra for the diastereomeric product mixture obtained after reaction of racemic model substrate material 9 with the chiral auxiliary reagent (S)-N-isopropyl-α-methylbenzylamine having conducted Step 1 in methylethylketone (MEK) and observed a significant stereoselective enhancement during the reaction, i.e. diastereomerically enhanced intermediate 11.

This reaction was conducted in a manner similar to that for Example 6 except that a two-fold excess of racemic 1,2-epoxy-3-phenoxypropane was utilized as the starting material. An NMR was obtained immediately after evaporation of the methanol. The key NMR region pertaining to the N-isopropyl system was appropriate for the material as a mixture of the two possible diastereomers which were obtained in about a 90% overall yield and having a 7% diastereomeric excess of the (S),(S)-product over the (R),(S)-product based upon calculations from the No spectrum (FIG. 2). Triplicate repetition of this reaction led to very similar results even when further purified by column chromatography.

EXAMPLE 9

Examination of Stereochemical Purification of the Diastereomeric Mixture Obtained in Example 8 by Physical Methods (Step 2)

A portion of the free amine oil was chromatographed according to the procedure described in Example 6. No quick separation of the two diastereomers was observed according to TLC analysis of every fraction and NMR analyses of grouped fractions. TLC was conducted on silica gel plates impregnated with a fluorescence indicator using development in methylene chloride: ethyl acetate: 28% aqueous $NH_3$ (20:1:0.1). $R_f$ values for both diastereomers were ca. 0.5 when visualized by UV irradiation. Another separate portion of the free amine oil was converted to the HCl salt form according to the procedure described in Example 4. In this case, however, crystalline materials were not readily obtained from solutions of methanol:ether at various ratios and at various lowered temperatures.

EXAMPLE 10

Debenzylation of the Diastereomeric Mixture Obtained in Example 8 (Step 3)

300 mg of the diastereomeric amine mixture obtained in Example 8 as the hydrochloride salts were dissolved in 25 ml of methanol and shaken in a Parr Apparatus with 20 mg of 10% Pd on carbon under 15 psi of hydrogen gas at room temperature for 20 minutes. Aliquots were removed at 5 minute intervals, filtered and evaporated to assess alteration in the key NMR region which would be reflective of any diastereomeric preference toward debenzylation. The reaction demonstrated only a very subtle preference (4% increase in diastereomeric excess of the (S),(S)-isomer) toward cleavage of the (R),(S)-isomer at the first 5 minute interval and then quickly went on to debenzylate both species completely by 20 minutes. Workup involved filtration of catalyst and evaporation of methanol followed by recrystallization from a minimal amount of methanol:ether according to Example 3. A nearly quantitative yield of product was obtained which had an NMR comparable to that of the racemic material from Example 3. exactly as would be expected in this step for all of the enantiomerically-related species which result from removal of the auxiliary chiral center.

EXAMPLE 11

Strategic Assessment Stop Point

Figure 1:
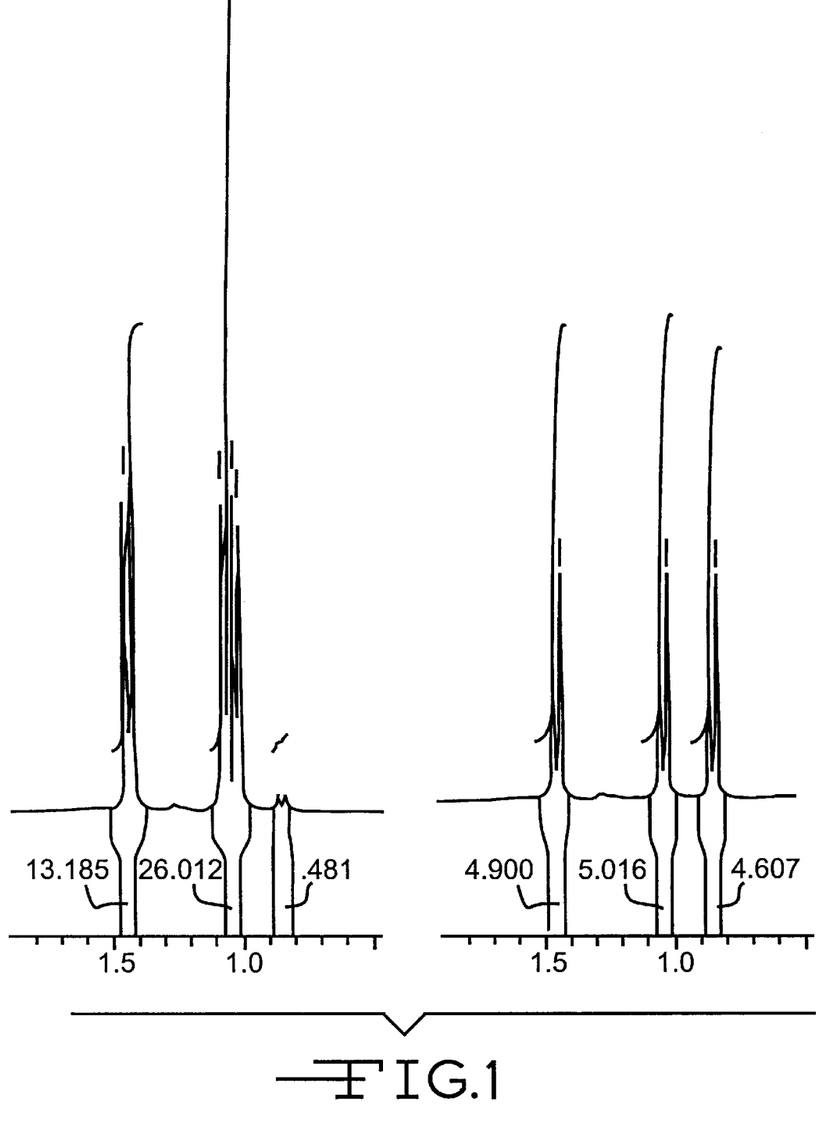
FIG. 1 displays the region of the NMR spectra which is significantly different between two stereo chemically defined diastereomer model standards of intermediate 11, namely pure (S), (S)-2-hydroxy-3-[[N-isopropyl-N-(α-methyl)benzyl]amino]propoxybenzene and the pure (R),(S)-isomer for the same composition.

Comparison of the stereochemical enhancements obtained at each of the Steps 1, 2 and 3A as demonstrated by the forgoing Examples 8, 9 and 10 respectively, suggests that the highest potential for the case in hand appears to reside at Step 1, even though the latter was not dramatic in that it only produced a diastereomeric excess (D.E.) of about 7% in favor of the (S),(S)-diastereomer. The D.E. value can be calculated by the following equation after determining the ratios of each diastereomer present from the actual NMR experimental data (FIGS. 1 and 2):

$$D.E. = \frac{[(S),(S)] - [(R),(S)]}{[(S),(S)] + [(R),(S)]} \times 100\%.$$

Nevertheless, the diastereomer being enriched in this case is the one which is desired since it is the (S),(S)-diastereomer which will eventually provide the (S)-enantiomer product. Thus, at this point, additional experimentation was next focused upon examining the precise reaction conditions employed during Step 1 with an eye toward increasing the stereochemical enhancement while still using the (S)-form of the chiral auxiliary.

EXAMPLE 12

Reiteration of Example 8 (Step 1) Under Various Conditions

An exhaustive examination of the reaction condition variables associated with Step 1 would normally proceed at this point, including the deployment of more sophisticated reagent family members. By example, two alternate solvents are conveyed within the present examination. Example 8 was thus repeated twice except that in one of the new runs toluene was attempted and in the other new run methylethylketone (MEK) was employed as the solvent in place of methanol. All other conditions were held constant. For this substrate, the reaction was found to be too sluggish to be practically useful when employing toluene. Alternatively, the reaction rate behaved similar to methanol when utilizing MEK, although the overall yield was somewhat reduced. Remarkably, however, in the case of MEK, the diastereomeric bias was found to actually be doubled. Thus the D.E., upon only the second reiteration of optimizing Step 1 and while still using just one of the most simple members from the family of chiral reagents, in this particular instance already has quickly climbed past a 15% enrichment of the (S),(S)-isomer over the (R),(S)-isomer.

EXAMPLE 13

Verification of Model Chemistry Step 1 Results From Experimental Example 12 On Exact Esmolol Case Methyl 3-(p-Hydroxyphenyl) propionate. A solution of 3 g, (18 mmol) of 3-(p-hydroxyphenyl)propionic acid in 50 ml of anhydrous methanol containing 5 drops of conc. $H_2SO_4$ was heated to reflux for 72 hours in a Soxhlet Extractor charged with 2 gm of 3A molecular sieves. The reaction medium was then evaporated under reduced pressure and the resulting oil taken up in 10 ml of toluene and washed with three 5 ml portions of water. The toluene phase was then dried over $MgSO_4$ and evaporated under reduced pressure to provide 2.3 gm (70%) of a clear oil having an appropriate NMR spectrum and single spot TLC [$R_f$=0.5 on Si plates using toluene:methanol (9:1) as developer]. This material was used directly in the next step.

Racemic Methyl 3-[4-(2,3-epoxypropoxy)phenyl] propionate. A mixture of 2.28 gm (1.3 mmol) of methyl 3-(4-hydroxyphenyl)propionate, 2.63 gm (19 mmol) of $K_2CO_3$ and 3 ml (38 mmol) of racemic epichlorohydrin in 50 ml of acetone was stirred and heated to reflux for 20 hours. The reaction medium was then filtered and evaporated under reduced pressure. The resulting oil was taken up in 25 ml of toluene and washed consecutively with 75 ml $H_2O$, 2×50 ml 1N NaOH and 2×50 ml $H_2O$. The toluene phase was then dried over $MgSO_4$ and evaporated under reduced pressure to provide a clear oil which was further purified by vacuum distillation. The final yield of purified oil having appropriate NMR and IR spectra and a correct elemental analysis was 1.31 gm (44%): b.p. ca. 155_C. (~0.4 mm Hg).

Step 1. The experimental conditions utilized in Example 8 were exactly repeated except that racemic methyl 3-[4-(2,3-epoxypropoxy)phenyl]propionate was used as the substrate and MEK was employed as the solvent as was done in Example 12. Based upon examination of the NMR spectrum (Example 14), the results obtained in the esmolol case were essentially the same as those obtained in Example 12 when MEK was used as the reaction solvent; namely, significant enhancement of the proper (S),(S)-diastereomer that can eventually provide the desired (S)-enantiomeric version of esmolol.

EXAMPLE 14

Figure 4A:
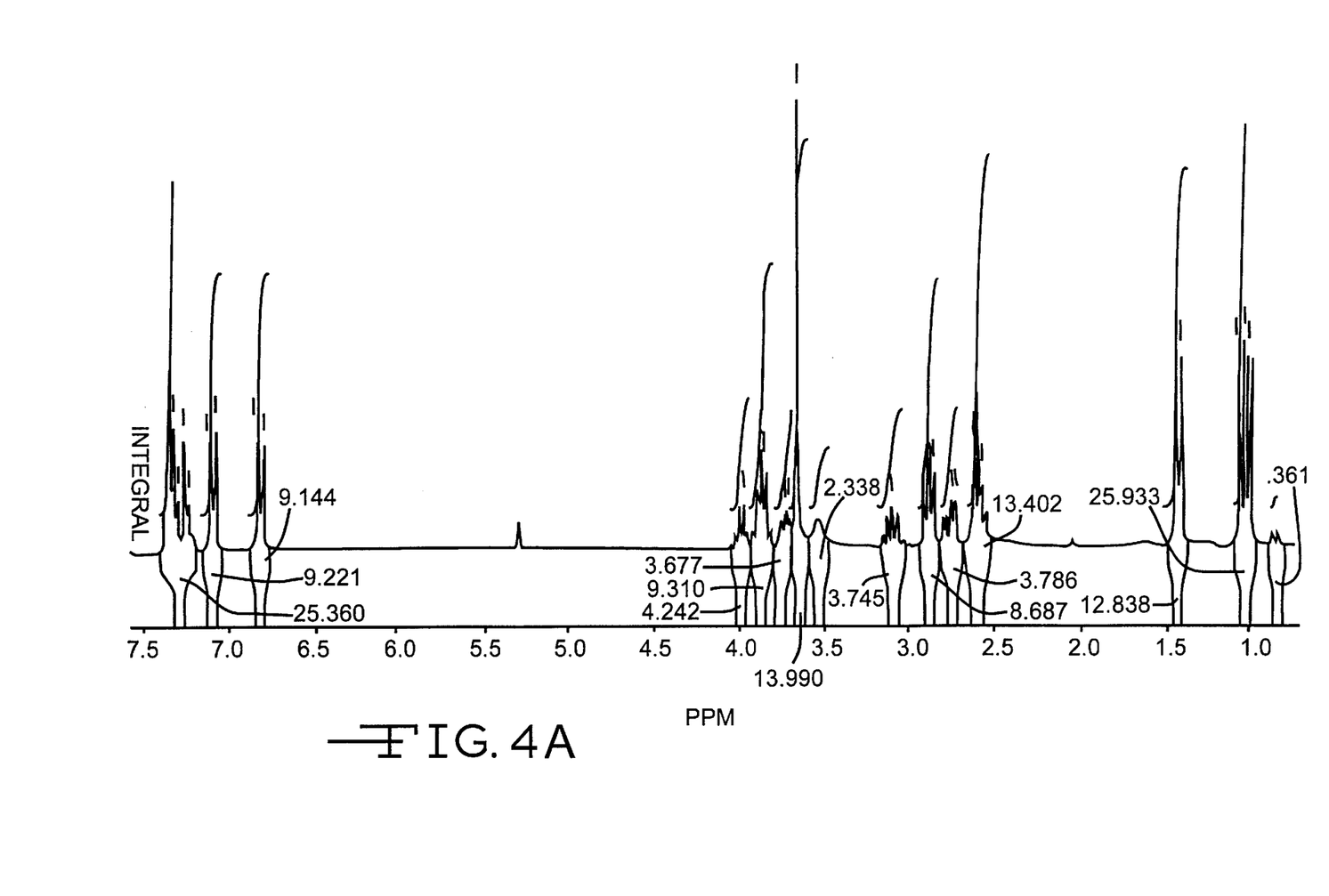
FIGS. 4A and 4B display the entire NMR spectra for two stereochemically defined diastereomer standards of intermediate 11, namely pure (S),(S)-methyl 3-[4-[2-hydroxy-3-[[N-isopropyl-N-((α-methyl)benzyl]amino]propoxy]phenyl]propionate and the pure (R),(S)-isomer for the same composition. The notable differences between these diastereomers in the alkyl region are similar to those which were blown-up for specific use within the model compounds in FIG. 1.
Figure 4B:
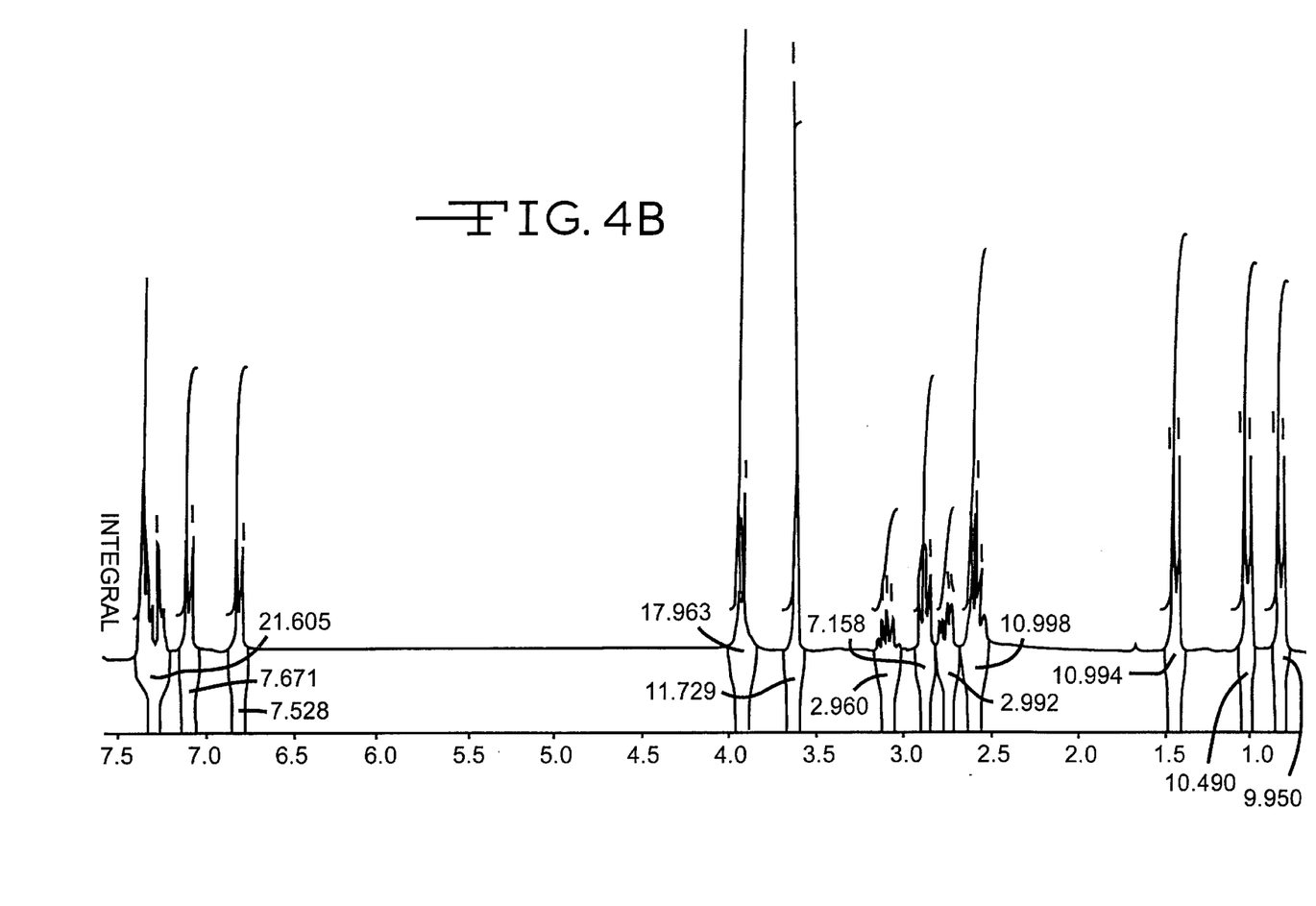

Preparation of Diastereomeric Standards For Use in the Esmolol Case During Assessment of NMR Spectra (FIGS. 4A and 4B)

(S),(S)-Methyl 3-[4-[2-Hydroxy-3-[[N-Isopropyl-N-(α-methyl)benzyl]amino]propoxy]phenyl]propionate A solution of 0.34 gm (1.45 mmol) of (S)-methyl 3-[4-(2,3-epoxypropoxy)phenyl]propionate (obtained by reacting methyl 3-(4-hydroxyphenyl)propionate (Example 13) with (S)-epichlorohydrin according to Example 13), and 0.28 gm (1.73 mmol) of (S)-N-isopropyl-α-methyl benzylamine (Example 4) in 5 ml of methanol was heated to reflux for 72 hours. The methanol was removed under reduced pressure to provide 0.64 gm of a crude oil which was further purified by column chromatography according to Example 6. 0.52 gm (90%) of a clear oil was obtained having appropriate NMR and IR spectra and correct elemental analysis data: b.p. 201–203_C. (0.5 mm Hg); $[\alpha]^{D25}=-19\_(c=0.2, MeOH)$.

(R),(S)-Methyl 3-[4-[2-Hydroxy-3-[[N-isopropyl-N-(α-methyl)benzyl]amino]propoxy]phenyl]propionate This material was prepared in a manner identical to that for the (S),(S)-diastereomer described above except that (R)-epichlorohydrin was utilized as the starting material according to Example 13. The pure material was obtained in 87% yield and had appropriate NMR and IR spectra and a correct elemental analysis: b.p. 183–185_C. (0.5 mm Hg); $[\alpha]^{D25}=+23\_(c=0.15, MeOH)$.

EXAMPLE 15

Debenzylation (Step 3) of the Enriched Diastereomeric Mixture Obtained in Example 13

Debenzylation was readily effected in a manner identical to that described in Example 10 except that the diastereomeric mixture obtained from Example 13 (hydrochloride salt form) was utilized as starting material and the reaction was run for 30 minutes under 30 psi of hydrogen. The reaction was essentially quantitative and upon workup, provided crystalline material having an NMR spectrum appropriate for the desired product.

The patents and documents referenced herein are hereby incorporated by reference.

Having described presently preferred embodiments of the present invention, the invention may be otherwise embodied within the scope of the appended claims.

What is claimed is:

1. A method of enhancing stereochemical purity of a product of chemical synthesis comprising the steps of:

providing a chiral α-substituted benzylamine reagent comprising wherein:

R=hydrogen, alkyl of from 1 to 10 carbons, aryl, aralkyl of from 6 to 20 carbons, or further functionalized versions of alkyl, aryl and aralkyl providing that said functional groups are not basic amines and when said groups are hydroxy, carboxy or other reactive functionalities that they are also protected in a manner that is common practice within the art;

*=a chiral carbon that is either pure (R) or pure (S) in its stereochemistry;

Ø=phenyl, para-methoxy phenyl, or (ortho-, para-)-dimethoxyphenyl;

R'=alkyl of from 1 to 10 carbons, aralkyl of from 6 to 20 carbons, carboxylic esters having alkyl adducts, carboxylic acid, hydroxy, and nitrogen-containing systems providing that said systems are not basic;

n=0 when R' is alkyl or aralkyl, or is 0 to 5 for all other embodiments of R' with the proviso that when R' is hydroxy or non-basic nitrogen-containing systems then n must be at least 1;

n'=1 or 2 and when 2 the second occurrence replaces the H depicted on the N and the two occurrences need not be identical in terms of Ø, R' and n, and that also in only this special circumstance, in one of the two occurrences both R' and n can be completely absent such that one of the two occurrences then simplifies to an unsubstituted benzyl group, to deliver a substituted or unsubstituted nitrogen atom during the chemical synthesis to enhance stereochemical purity of a product from the chemical synthesis; and then removing the α-substituted benzyl group from the chemical synthesis product by catalytic hydrogenolysis.

2. The method of claim 1 wherein R is no longer hydrogen.

3. The method of claim 1 wherein n' is equal to 2.

4. The method of claim 3 wherein R is no longer hydrogen.

5. The method of claim 1 wherein the chemical synthesis involves formation of pharmaceutically relevant materials having enhanced stereochemical purity.

6. The method of claim 1 wherein the chemical synthesis products are aryloxypropanolamines.

7. The method of claim 6 wherein said aryloxypropanolamines are two enantiomeric forms of esmolol.

* * * * *